United States Patent
Gimenez et al.

(10) Patent No.: US 11,612,276 B2
(45) Date of Patent: Mar. 28, 2023

(54) SANITIZING APPARATUS

(71) Applicants: Jorge Alberto Gimenez, Weston, FL (US); Deborah Medel-Gimenez, Weston, FL (US)

(72) Inventors: Jorge Alberto Gimenez, Weston, FL (US); Deborah Medel-Gimenez, Weston, FL (US)

( * ) Notice: Subject to any disclaimer, the term of this patent is extended or adjusted under 35 U.S.C. 154(b) by 37 days.

(21) Appl. No.: 17/404,794

(22) Filed: Aug. 17, 2021

(65) Prior Publication Data
US 2023/0056519 A1 Feb. 23, 2023

(51) Int. Cl.
| A47K 5/12 | (2006.01) |
| A61L 2/26 | (2006.01) |
| B65D 83/00 | (2006.01) |
| A61L 2/18 | (2006.01) |

(52) U.S. Cl.
CPC .............. *A47K 5/1201* (2013.01); *A61L 2/18* (2013.01); *A61L 2/26* (2013.01); *B65D 83/0072* (2013.01); *A61L 2202/15* (2013.01); *A61L 2202/182* (2013.01)

(58) Field of Classification Search
CPC . A47K 5/1201; A61L 2/18; A61L 2/26; A61L 2202/15; A61L 2202/182; B65D 83/0072
USPC .......... 222/95, 214, 386, 405; 401/205, 206, 401/188 R
See application file for complete search history.

(56) References Cited

U.S. PATENT DOCUMENTS

| 85,084 | A | * | 12/1868 | Gilroy | B65D 83/0005 222/386 |
| 344,447 | A | * | 6/1886 | Johnston | B65D 83/0005 222/386 |
| 385,916 | A | * | 7/1888 | David | B65D 83/0005 222/386 |
| 968,752 | A | * | 8/1910 | Ellis | B65D 83/0005 222/386 |
| 1,298,108 | A | * | 3/1919 | Sisti | B65D 23/06 222/110 |
| 1,315,305 | A | * | 9/1919 | Hegland | B43K 5/189 401/148 |

(Continued)

OTHER PUBLICATIONS

Gojo, Purell NXT Manual Hand Sanitizer Dispenser, https://www.gojo.com/en/Product/2120-06.

*Primary Examiner* — Frederick C Nicolas
*Assistant Examiner* — Michael J. Melaragno

(57) ABSTRACT

A sanitizing apparatus includes a main housing, a dispensing member, a supporting platform, and a sanitizing fluid pouch. the main housing comprises a front wall, a first sidewall, a second sidewall, a rear wall, a bottom wall, and an opening. The front wall, the first sidewall, the second sidewall, the rear wall, the bottom wall of the main housing together form an internal space accessible through the opening of the main housing. The dispensing member is inserted into the internal space through the opening of the main housing. The dispensing member comprises a dispensing mechanism. The sanitizing fluid pouch is filled with a sanitizing fluid and is flexible and deformable. The supporting platform is placed within the dispensing member. The supporting platform comprises a supporting plate on which is seated the sanitizing fluid pouch. The supporting platform further comprises a pressure-applying member.

20 Claims, 11 Drawing Sheets

(56) References Cited

U.S. PATENT DOCUMENTS

| | | | | |
|---|---|---|---|---|
| 1,504,001 | A * | 8/1924 | Soyez | A21B 5/04 401/175 |
| 1,509,219 | A * | 9/1924 | Alexander | B65D 47/42 15/231 |
| 1,737,294 | A * | 11/1929 | Booty | A45D 33/04 132/299 |
| 1,919,887 | A * | 7/1933 | Gleeson | A45D 40/26 206/385 |
| 1,929,884 | A * | 10/1933 | Fisher | A47L 25/08 222/548 |
| 1,942,248 | A * | 1/1934 | Kemp | B65D 83/0027 222/405 |
| 2,180,506 | A * | 11/1939 | Burbig | B65D 47/44 401/206 |
| 2,500,687 | A * | 3/1950 | Kamp | A45D 40/0075 222/386 |
| 2,659,517 | A * | 11/1953 | Reinhardt, Jr. | A47K 5/1211 222/326 |
| 2,925,147 | A * | 2/1960 | Minera | F16N 11/04 184/45.1 |
| 3,244,333 | A * | 4/1966 | Kohn | A45D 40/0075 277/645 |
| 3,377,003 | A * | 4/1968 | Bacon | B65D 83/64 222/386 |
| 3,393,963 | A * | 7/1968 | Nadai | B65D 47/42 401/207 |
| 3,561,644 | A * | 2/1971 | Works | B65D 83/62 222/95 |
| 3,661,468 | A * | 5/1972 | Schwartzman | B65D 47/42 401/206 |
| 3,805,990 | A * | 4/1974 | Palaudarias | B65D 47/248 251/339 |
| 4,193,513 | A * | 3/1980 | Bull, Jr. | G01F 11/02 222/105 |
| 5,037,010 | A * | 8/1991 | Dikstein | A45D 40/0075 222/405 |
| 5,148,951 | A * | 9/1992 | Moure | B65D 83/00 425/84 |
| 5,513,778 | A * | 5/1996 | Cardia | A45D 40/0075 222/386 |
| 5,685,456 | A * | 11/1997 | Goldstein | B05B 9/0838 222/340 |
| 6,231,259 | B1 * | 5/2001 | Murgida | A61K 8/895 401/175 |
| 6,234,698 | B1 * | 5/2001 | De Laforcade | B65D 83/285 401/175 |
| 6,457,893 | B1 * | 10/2002 | Hamilton | A45D 34/04 401/148 |
| 6,499,898 | B1 * | 12/2002 | Garcia | B05C 17/002 401/265 |
| 6,533,482 | B1 * | 3/2003 | Byun | B05B 11/3004 401/265 |
| 6,688,795 | B1 * | 2/2004 | Jacob | B65D 47/42 401/262 |
| 7,316,332 | B2 | 1/2008 | Powers | |
| 7,441,974 | B2 * | 10/2008 | Gueret | B65D 47/42 401/205 |
| 7,722,276 | B2 * | 5/2010 | Gueret | B65D 47/42 401/206 |
| 8,226,317 | B2 * | 7/2012 | Uxa, Jr. | A47K 7/03 401/265 |
| 8,294,585 | B2 | 10/2012 | Barnhill | |
| 8,821,059 | B2 * | 9/2014 | Sasaki | B65D 47/04 401/133 |
| 9,060,655 | B2 | 6/2015 | Iseri | |
| 2001/0031171 | A1 * | 10/2001 | Delage | A45D 34/042 401/196 |
| 2002/0170929 | A1 * | 11/2002 | Bettinger | G01F 11/021 222/386 |
| 2003/0024949 | A1 * | 2/2003 | Garcia | B65D 83/0072 222/546 |
| 2003/0170067 | A1 * | 9/2003 | Reggiani | B65D 83/285 401/206 |
| 2003/0202838 | A1 * | 10/2003 | Sun | A45D 34/042 401/196 |
| 2004/0118879 | A1 * | 6/2004 | Konietzko | B65D 83/0005 222/386 |
| 2005/0048048 | A1 * | 3/2005 | Valenzuela | A61K 33/00 424/125 |
| 2005/0135867 | A1 * | 6/2005 | Gueret | A45D 34/04 401/196 |
| 2006/0228155 | A1 | 10/2006 | Butler | |
| 2007/0110506 | A1 * | 5/2007 | Erickson | A61M 35/003 401/205 |
| 2007/0262091 | A1 | 11/2007 | Harper | |
| 2008/0035670 | A1 * | 2/2008 | Timmann | A61L 9/12 222/386 |
| 2008/0166174 | A1 * | 7/2008 | Kennedy | B05C 17/002 401/206 |
| 2008/0280187 | A1 * | 11/2008 | Sadamoto | H01M 8/04 222/95 |
| 2009/0001102 | A1 * | 1/2009 | Fang | B65D 83/0044 222/405 |
| 2009/0159487 | A1 | 6/2009 | Tacoma | |
| 2011/0297704 | A1 * | 12/2011 | Esteve | A45D 34/00 222/405 |
| 2012/0080451 | A1 | 4/2012 | Williams | |
| 2012/0111894 | A1 * | 5/2012 | Bakhos | B65D 47/2018 222/386.5 |
| 2013/0334248 | A1 | 12/2013 | Iseri | |
| 2016/0157581 | A1 * | 6/2016 | Kim | B65D 83/0033 222/386 |

* cited by examiner

SANITIZING APPARATUS

FIELD OF THE INVENTION

The present invention relates generally to sanitizing apparatuses. More specifically, the present invention is a sanitizing apparatus that delivers sanitizing fluids to fingertips. The present invention is specifically designed for sanitizing the fingertips of a user. However, the present invention is not limited to this option, and it may further be adapted for different purposes.

BACKGROUND OF THE INVENTION

The origin of the modern keyboard as the primary method for inputting text and data from a human to a machine dates back to early typewriters in the 19th century. As computers were developed, it was a natural evolution to adapt the typewriter keyboard to be used as the primary method for inputting text and data. Computers, and their accompanying keyboards, have become pervasive in environments across numerous industries.

Because of the mechanical nature of the keys on traditional keyboards, they contain many moving parts that result in cracks and cavities where dust and contamination can collect. Furthermore, studies have shown that there are about 2 to 10 million bacteria on people's fingertips. Fingertips are repeatedly in contact with keyboards, transporting the bacteria and other infectious agents (e.g., viruses, etc.) from fingertips to keyboards, and vice versa. Moreover, as electronic devices become ubiquitous, people are increasingly required to touch the input devices of the electronic devices, such as keypads and/or touchscreens of Point of Sale (POS) terminal and/or Automated Teller Machines (ATMs). People often choose to use a hand sanitizer, which is typically in the form of a sprayer, after using keyboards. However, hand sanitizers are usually not easily accessible, and the fingertips that are frequently in contact with keyboards cannot be effectively cleaned.

Therefore, it is an objective of the present invention to provide a sanitizing apparatus that overcomes the problems set forth above. The present invention is a sanitizing apparatus that allows a user to clean and sanitize his/her fingertips in a convenient and easy manner.

SUMMARY OF THE INVENTION

The present invention discloses a sanitizing apparatus that comprises a main housing, a dispensing member, a supporting platform, and a sanitizing fluid pouch. The main housing comprises a front wall, a first sidewall, a second sidewall, a rear wall, a bottom wall, and an opening. The front wall, the first sidewall, the second sidewall, the rear wall, the bottom wall of the main housing together form an internal space accessible through the opening of the main housing. The dispensing member is inserted into the internal space through the opening of the main housing. The dispensing member comprises a dispensing mechanism. The sanitizing fluid pouch is filled with a sanitizing fluid and is flexible and deformable. The supporting platform is placed within the dispensing member. The supporting platform comprises a supporting plate on which is seated the sanitizing fluid pouch. The supporting platform further comprises a pressure-applying member that applies pressure to the supporting platform and thus the sanitizing fluid pouch.

One or more of the following features may be included. The dispensing member comprises a top portion, a neck portion, and a body portion. The top portion comprises a top opening, and the dispensing mechanism is disposed on the top opening. The neck portion comprises an attachment mechanism that securely attaches the dispensing member to the main housing, the attachment mechanism comprising a reduced dimension relative to the body portion. The dispensing mechanism is a piece of porous fabric. The body portion comprises a front wall, a first sidewall, a second sidewall, and a rear wall, which together form a channel, the top opening being smaller than the cross-section of the channel. At least one of the front wall, the first sidewall, the second sidewall, and the rear wall of the main housing comprises a first slit, and at least one of the front wall, the first sidewall, the second sidewall, and the rear wall of the dispensing member comprises a second slit that is aligned with the first slit. At least one of the front wall, the first sidewall, the second sidewall, and the rear wall of the main housing is transparent, and at least a corresponding one of the front wall, the first sidewall, the second sidewall, and the rear wall of the dispensing member is transparent. The pressure-applying member comprises a spring that at one end connects to the supporting plate and at the other end connects to the bottom wall of the main housing.

BRIEF DESCRIPTION OF THE DRAWINGS

The accompanying drawings, which are included to provide a further understanding of the invention, are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the present invention. That is, the dimensions of the components of the present invention, independently and in relation to each other can be different. It should be noted that the drawings are schematic and not necessarily drawn to scale. Some drawings are enlarged or reduced to improve drawing legibility.

DETAIL DESCRIPTIONS OF THE INVENTION

Figure 1:
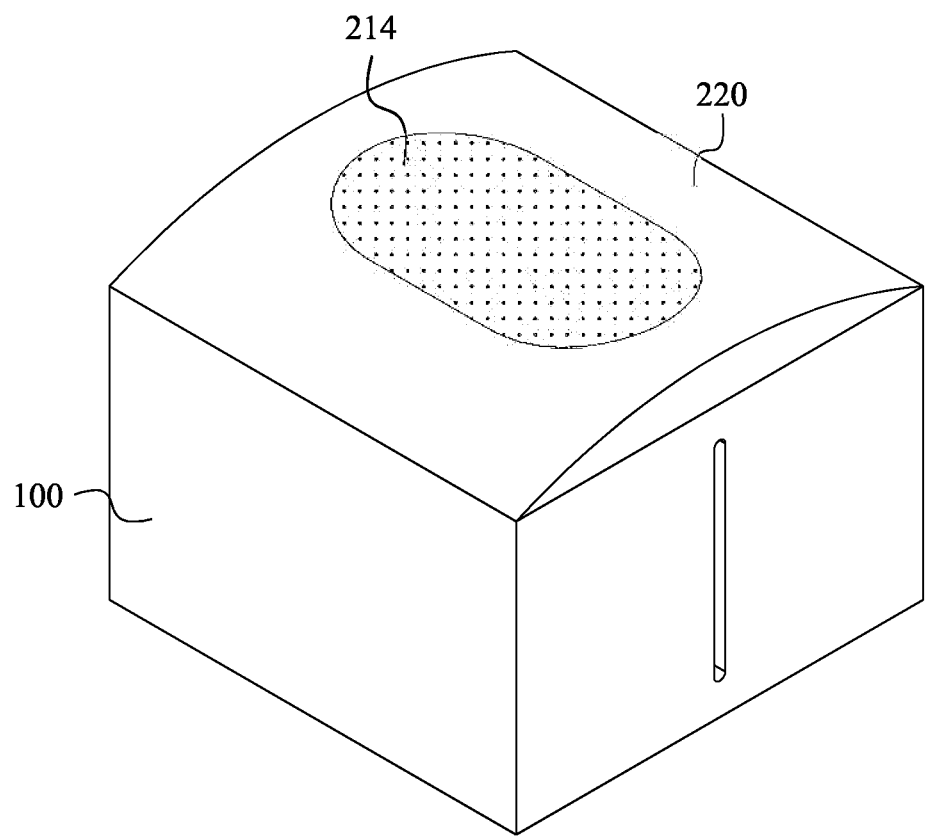
FIG. 1 depicts a perspective of the present invention.
Figure 2:
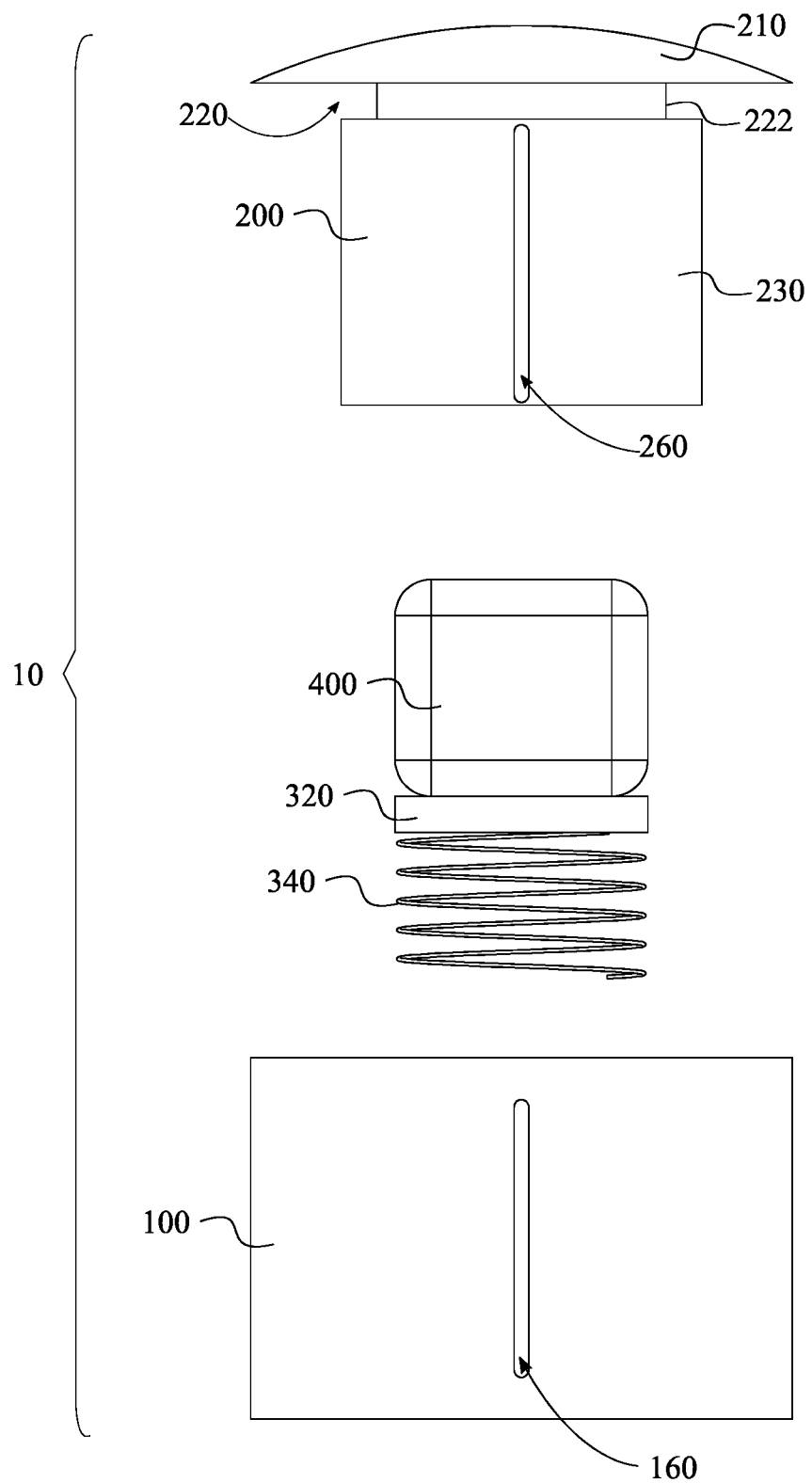
FIG. 2 depicts an exploded view of the present invention.
Figure 3:
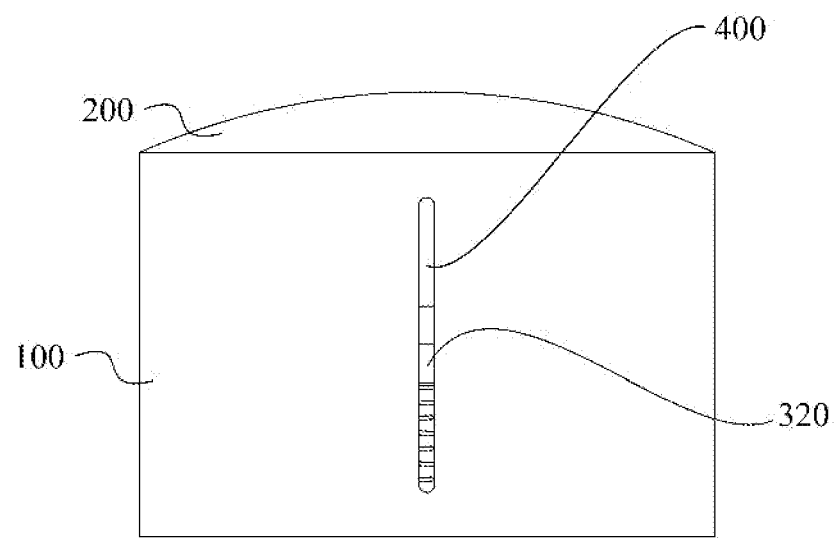
FIG. 3 depicts a front view of the present invention, wherein a sanitizing pouch is full of sanitizing fluid.
Figure 4:
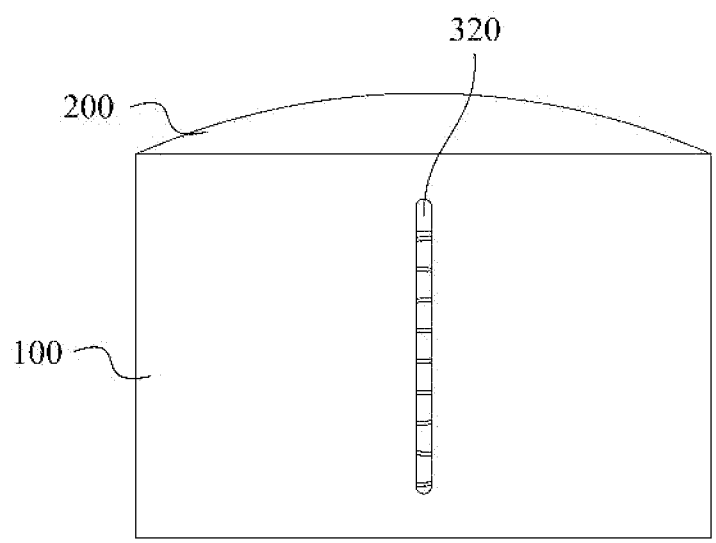
FIG. 4 depicts a front view of the present invention, wherein the sanitizing fluid in the sanitizing pouch is nearly depleted.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and is made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. When not explicitly defined herein, to the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subject matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise indicated, the drawings are intended to be read together with the specification and are to be considered a portion of the entire written description of this invention. As used in the following description, the terms "horizontal", "vertical", "left", "right", "up", "down" and the like, as well as adjectival and adverbial derivatives thereof (e.g., "horizontally", "rightwardly", "upwardly", "radially", etc.), simply refer to the orientation of the illustrated structure as the particular drawing figure faces the reader. Similarly, the terms "inwardly," "outwardly" and "radially" generally refer to the orientation of a surface relative to its axis of elongation, or axis of rotation, as appropriate. As used herein, the term "proximate" refers to positions that are situated close/near in relationship to a structure. As used in the following description, the term "distal" refers to positions that are situated away from positions.

The present disclosure includes many aspects and features. Moreover, while many aspects and features relate to, and are described in the context of sanitizing apparatus, embodiments of the present disclosure are not limited to use only in this context.

The present invention is a sanitizing apparatus that is specifically designed to sanitize fingertips of a user. It is an aim of the present invention to provide a sanitizing apparatus that allows a user's fingertips to be sanitized conveniently. It is another aim of the present invention to provide a sanitizing apparatus that is simple in structure, inexpensive to manufacture, and easy to use. It is yet another aim of the present invention to provide a compact sanitizing apparatus that can be easily carried around. The present invention may be used after using keyboards, counting of money, or other activities where the fingertips may be in contact with an unhygienic surface.

Referring now to the figures of the present disclosure. FIG. 1 is a perspective view illustrating the present invention. The sanitizing apparatus 10 of the present invention comprises a main housing 100, a dispensing member 200, a supporting platform 300, and a sanitizing fluid pouch 400.

In reference to FIGS. 1-7, the main housing 100 is configured to house other components of the present invention. It should be noted that the main housing 100 can be of any shape, size, material, features, type or kind, orientation, location, quantity, components, and arrangements of components that would allow the present invention to fulfill the objectives and intents of the present invention. In a preferred embodiment, the main housing 100 takes the shape of a cuboid, defining a front wall 110, a first sidewall 112, a second sidewall 114, a rear wall 116, and a bottom wall 118. Moreover, the top of the main housing 100 may comprise an opening 140 through which the dispensing member 200, the supporting platform 300, and the sanitizing fluid pouch 400 may be inserted. Preferably, the length of the first sidewall 112 or the second sidewall 114 is greater than that of the front wall 110 or the rear wall 116. An internal space 120 is formed by the front wall 110, the first sidewall 112, the second sidewall 114, the rear wall 116, and the bottom wall 118, so as to accommodate the dispensing member 200, the supporting platform 300, and the sanitizing fluid pouch 400. The internal space 120 may be accessible via the opening 140. In a preferred embodiment, the front wall 110 comprises a slit or a window 160 through which the user can observe the inside supporting platform 300. In another embodiment, the front wall 110 may be transparent, instead of comprising a slit 160.

In reference to FIGS. 1-6 and 8-10, the dispensing member 200 is configured to dispense the sanitizing fluid from the sanitizing fluid pouch 400 to a user's fingertip. It should be noted that the dispensing member 200 can be of any shape, size, material, features, type or kind, orientation, location, quantity, components, and arrangements of components that would allow the present invention to fulfill the objectives and intents of the present invention. In a preferred embodiment, the dispensing member 200 comprises a top portion 210, a neck portion 220, and a body portion 230. In the illustrated embodiment, the top portion 210 is arch-shaped for aesthetic purposes. In another embodiment, the top portion 210 may also be shaped like a dome. A top opening 212 is formed substantially at the center of the top portion 210. In a preferred embodiment, a dispensing mechanism 214 is arranged at the top opening 212. Preferably, the dispensing mechanism 214 may be a membrane that is a piece of porous fabric so as to allow the sanitizing fluid to pass under pressure. When a user presses the dispensing mechanism 214 using his/her fingertip, increased pressure is applied to the sanitizing fluid pouch 400 by the fingertip together with the supporting platform 300, forcing the sanitizing fluid out through the dispensing mechanism 214.

Figure 5:
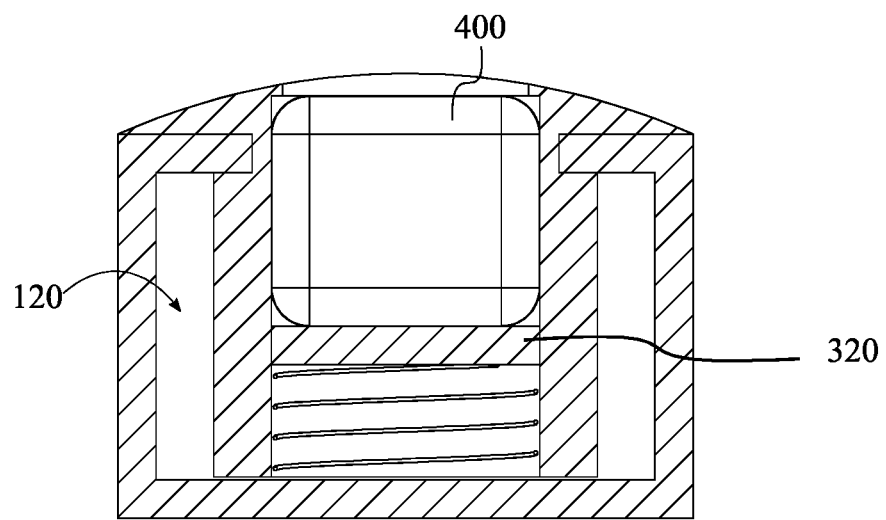
FIG. 5 depicts a cross-sectional view illustrating the internal structure of the present invention, wherein the sanitizing pouch is full of sanitizing fluid.
Figure 6:
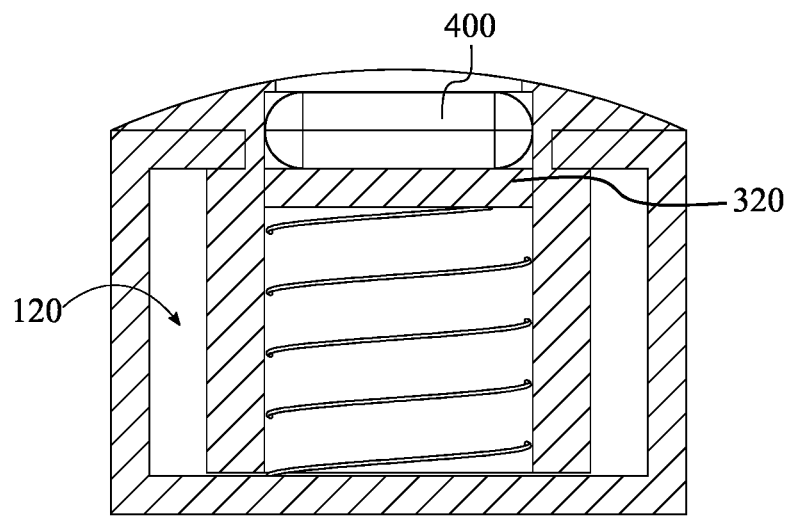
FIG. 6 depicts a cross-sectional view illustrating the internal structure of the present invention, wherein the sanitizing fluid in the sanitizing pouch is nearly depleted.
Figure 7:
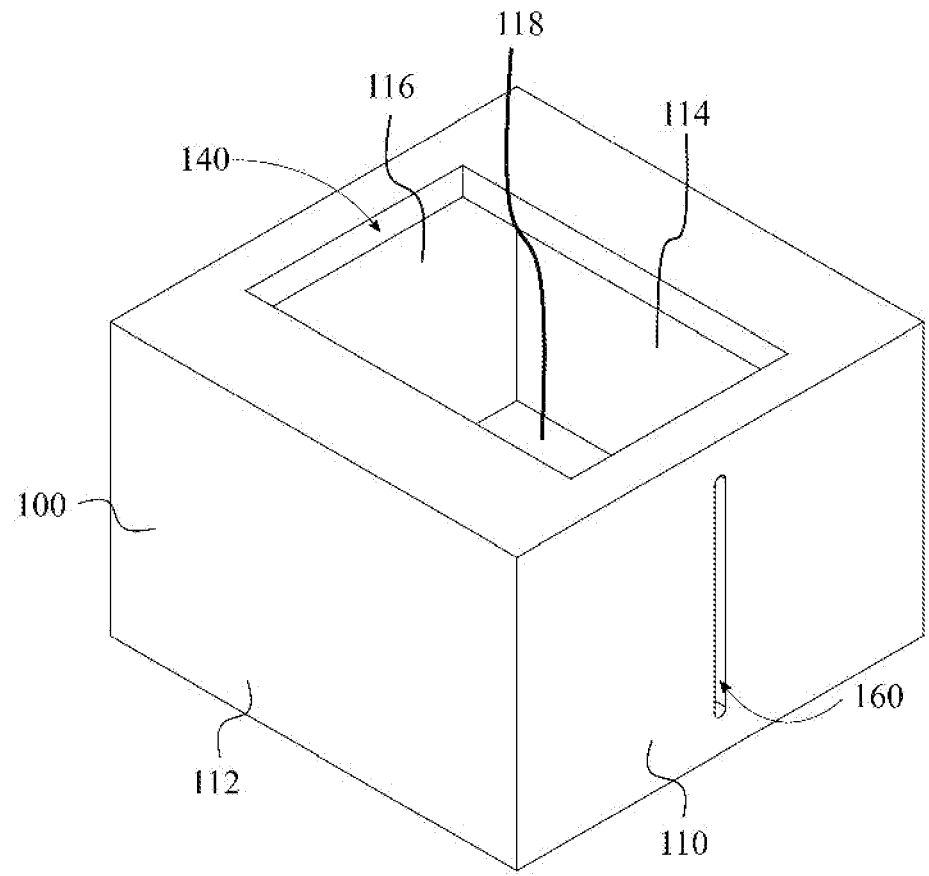
FIG. 7 depicts a perspective view of a main housing the present invention.
Figure 8:
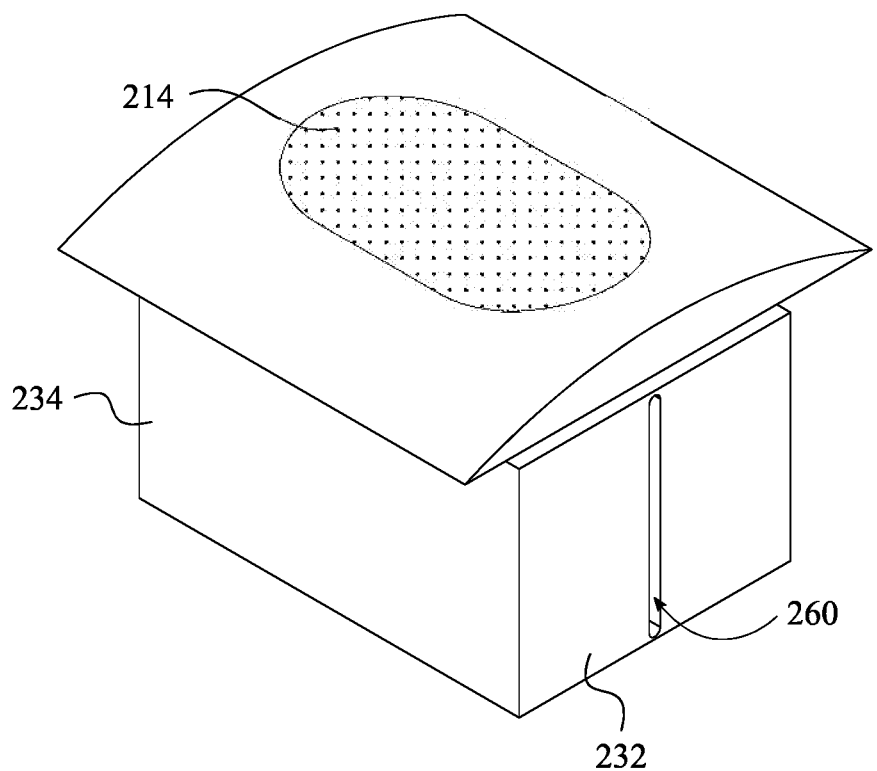
FIG. 8 depicts a perspective view of a dispensing member of the present invention.
Figure 9:
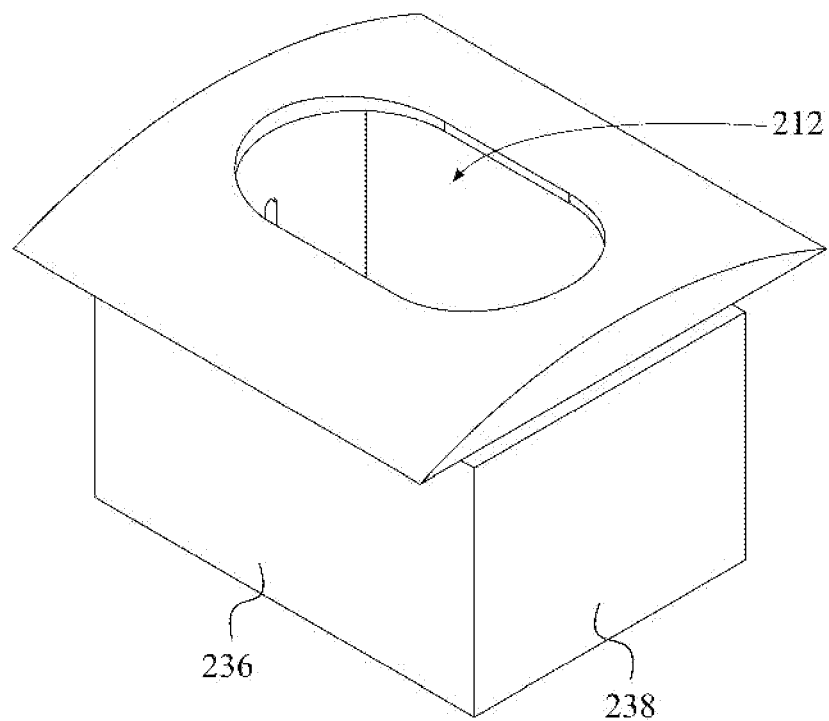
FIG. 9 depicts another perspective view of the dispensing member of the present invention.
Figure 10:
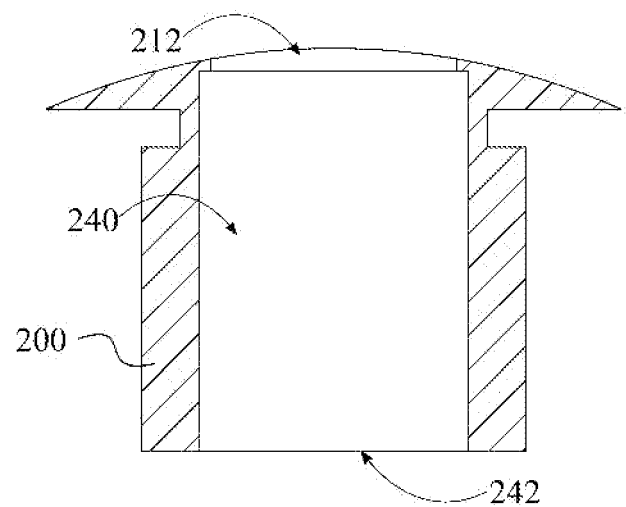
FIG. 10 depicts a cross-sectional view illustrating the internal structure of the dispensing member of the present invention.
Figure 11:
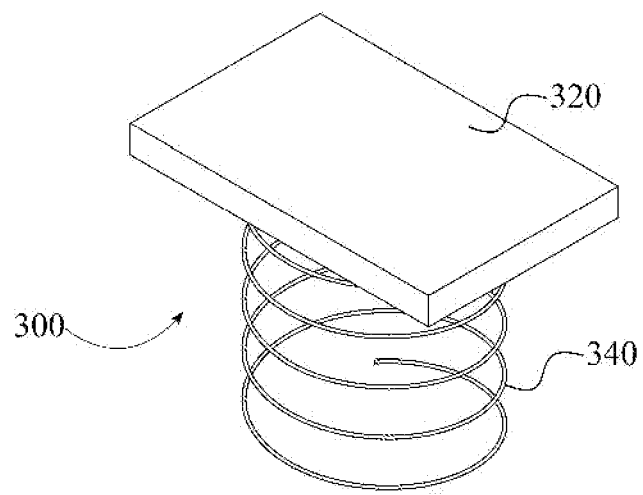
FIG. 11 depicts a perspective view of a supporting platform of the present invention.

The neck portion 220 comprises an attachment mechanism 222 that attaches the dispensing member 200 to the main housing 100. In the illustrated embodiment, the attachment mechanism 222 comprise a reduced dimension such that the neck portion 220 may be snapped onto the edge of the opening 140 of the main housing 100, as best shown in FIGS. 5-6. In other embodiment, other types of attachment mechanism may be used to securely attach the dispensing member 200 to the main housing 100. For example, the dispensing member 200 may be magnetically attached, glued, or otherwise clamped to the main housing 100.

The body portion 230 is configured to house the supporting platform 300 together with the sanitizing fluid pouch 400. Preferably, the body portion 230 comprises a cross-section corresponding to the shape of the opening 140 of the main housing 100 such that the body portion 230 can be inserted through the opening 140 of the main housing 100. The body portion 230 may comprise a front wall 232, a first sidewall 234, a second sidewall 236, and a rear wall 238, which together form a channel 240. The channel 240 comprises a bottom opening 242 through which the supporting platform 300 and the sanitizing fluid pouch 400 may be inserted. It should be understood that the top opening 212 is preferably slightly smaller than the cross-section of the channel 240 such that the sanitizing fluid pouch 400 can be retained between the dispensing mechanism 214 and the supporting platform 300. A slit 260 may be provided on the front wall 232 of the body portion 230 of the dispensing member 200, corresponding to the slit 160 on the main housing 100. In this way, users may observe the position of the supporting platform 300, thereby deciding when to replace the sanitizing fluid pouch 400. In one embodiment, similar to a transparent front wall 110 of the main housing 100, the front wall 232 may also be transparent, eliminating the necessity of using the slit 260. More generally, at least one of the front wall 110, the first sidewall 112, the second sidewall 114, and the rear wall 116 of the main housing 100 may comprise a slit 160, and at least one of the front wall 232, the first sidewall 234, the second sidewall 236, and the rear wall 238 of the dispensing member 200 may comprise a slit 260. The slit 160 of the main housing 100 and the slit 260 of the dispensing member 200 may be aligned with each other. Alternatively, at least one of the front wall 110, the first sidewall 112, the second sidewall 114, and the rear wall 116 of the main housing 100 and at least a corresponding one of the front wall 232, the first sidewall 234, the second sidewall 236, and the rear wall 238 of the dispensing member 200 may be made from transparent materials.

In reference to FIGS. 2-6 and 11, the supporting platform 300 is configured to support the sanitizing fluid pouch 400 and apply suitable pressure to the sanitizing fluid pouch 400. It should be noted that the supporting platform 300 can be of any shape, size, material, features, type or kind, orientation, location, quantity, components, and arrangements of components that would allow the present invention to fulfill the objectives and intents of the present invention. Preferably, the supporting platform 300 is located inside the channel 240. In a preferred embodiment, the supporting platform 300 comprises a supporting plate 320 and a pressure-applying member 340. In a preferred embodiment, the supporting plate 320 is colored in red or other vivid colors to facilitate observation of the supporting plate 320. The supporting plate 320 comprises a top surface on which the sanitizing fluid pouch 400 is placed and a bottom surface to which one end of the pressure-applying member 340 is connected. The other end of the pressure-applying member 340 is connected to the bottom wall 118 of the main housing 100. The shape of the supporting plate 320 preferably conforms to that of the cross-section of the channel 240. Moreover, the dimensions of the supporting plate 320 are slightly smaller than the channel 240, such that the supporting plate 320 may reciprocally travel in the channel 240. In one embodiment, the pressure-applying member 340 is a spring. The pressure-applying member 340 is configured to apply a suitable pushing force onto the supporting plate 320 and thus the sanitizing fluid pouch 400 in a manner that substantially no sanitizing fluid is forced out if the user does not press the dispensing mechanism 214 and the compression of the fingertip of the user and the pressure-applying member 340 causes a predetermined amount of sanitizing fluid to dispense. Although a spring is used in the illustrated embodiment, it should be noted that other types of mechanisms may be utilized to exert the pushing force on the supporting plate 320 and thus the sanitizing fluid pouch 400.

The sanitizing fluid pouch 400 is configured to hold sanitizing fluid therein. It should be noted that the sanitizing fluid pouch 400 can be of any shape, size, material, features, type or kind, orientation, location, quantity, components, and arrangements of components that would allow the present invention to fulfill the objectives and intents of the present invention. In a preferred embodiment, the sanitizing fluid pouch 400 is flexible and deformable, such that the position of the supporting plate 320 may change as the sanitizing fluid depletes. In this way, proper pressure onto the sanitizing fluid pouch is maintained throughout the use of the sanitizing fluid pouch 400. The sanitizing fluid may include any fluid having sterilizing, disinfecting, antiseptic, antimicrobial, and/or other sanitizing or cleaning properties. Preferably, the top surface of the sanitizing fluid pouch 400 may be made from the same material as that of the dispensing mechanism 214, such that the sanitizing fluid will be forced out from the top surface of the sanitizing fluid pouch 400 when the sanitizing fluid pouch 400 is compressed. In one embodiment, the sanitizing fluid pouch 400 is designed to be replaceable.

It is envisioned that the sizes of the components forming the present invention such as the main housing 100, the dispensing member 200, the supporting platform 300, and/or the sanitizing fluid pouch 400 can vary based on design requirements.

Although the disclosure has been explained in relation to its preferred embodiment, it is to be understood that many other possible modifications and variations can be made without departing from the spirit and scope of the disclosure.

What is claimed is:

1. A sanitizing apparatus comprising:
a main housing;
a dispensing member;
a supporting platform;
a sanitizing fluid pouch;
the main housing comprising a front wall, a first sidewall, a second sidewall, a rear wall, a bottom wall, and an opening;
the front wall, the first sidewall, the second sidewall, the rear wall, the bottom wall of the main housing together forming an internal space accessible through the opening of the main housing;
the dispensing member being inserted into the internal space through the opening of the main housing;
the dispensing member comprising a dispensing mechanism;
the sanitizing fluid pouch being filled with a sanitizing fluid;
the sanitizing fluid pouch being flexible and deformable;
the supporting platform being placed inside the dispensing member;
the supporting platform comprising a supporting plate on which is seated the sanitizing fluid pouch; and
the supporting platform further comprising a pressure-applying member that applies pressure to the supporting platform and thus the sanitizing fluid pouch.

2. The sanitizing apparatus as claimed in claim 1, wherein the dispensing member comprises a top portion, a neck portion, and a body portion.

3. The sanitizing apparatus as claimed in claim 2, wherein the top portion comprises a top opening, and the dispensing mechanism is disposed on the top opening.

4. The sanitizing apparatus as claimed in claim 2, wherein the neck portion comprises an attachment mechanism that securely attaches the dispensing member to the main housing;
the attachment mechanism comprising a reduced dimension relative to the body portion.

5. The sanitizing apparatus as claimed in claim 3, wherein the dispensing mechanism is a piece of porous fabric.

6. The sanitizing apparatus as claimed in claim 3, wherein the body portion comprises a front wall, a first sidewall, a second sidewall, and a rear wall, which together form a channel;
the top opening being smaller than the cross-section of the channel.

7. The sanitizing apparatus as claimed in claim 6, wherein at least one of the front wall, the first sidewall, the second sidewall, and the rear wall of the main housing comprises a first slit, and at least one of the front wall, the first sidewall, the second sidewall, and the rear wall of the dispensing member comprises a second slit that is aligned with the first slit.

8. The sanitizing apparatus as claimed in claim 6, wherein at least one of the front wall, the first sidewall, the second sidewall, and the rear wall of the main housing is transparent, and at least a corresponding one of the front wall, the first sidewall, the second sidewall, and the rear wall of the dispensing member is transparent.

9. The sanitizing apparatus as claimed in claim 1, wherein the pressure-applying member comprises a spring that at one end connects to the supporting plate and at the other end connects to the bottom wall of the main housing.

10. A sanitizing apparatus comprising:
a main housing;
a dispensing member;
a supporting platform;
a sanitizing fluid pouch;
the main housing comprising a front wall, a first sidewall, a second sidewall, a rear wall, a bottom wall, and an opening;
the front wall, the first sidewall, the second sidewall, the rear wall, the bottom wall of the main housing together forming an internal space accessible through the opening of the main housing;
the dispensing member being inserted into the internal space through the opening of the main housing;
the dispensing member comprising a dispensing mechanism;
the sanitizing fluid pouch being filled with a sanitizing fluid;
the sanitizing fluid pouch being flexible and deformable;
the supporting platform being placed within the dispensing member;
the supporting platform comprising a supporting plate on which is seated the sanitizing fluid pouch;
the supporting platform further comprising a spring that at one end connects to the supporting plate and at the other end connects to the bottom wall of the main housing; and
the spring being pressed between the supporting plate and the bottom wall of the main housing to apply pressure to the supporting platform and thus the sanitizing fluid pouch.

11. The sanitizing apparatus as claimed in claim 10, wherein the dispensing member comprises a top portion, a neck portion, and a body portion.

12. The sanitizing apparatus as claimed in claim 11, wherein the top portion comprises a top opening, and the dispensing mechanism is disposed on the top opening.

13. The sanitizing apparatus as claimed in claim 11, wherein the neck portion comprises an attachment mechanism that securely attaches the dispensing member to the main housing;
the attachment mechanism comprising a reduced dimension relative to the body portion.

14. The sanitizing apparatus as claimed in claim 12, wherein the dispensing mechanism is a piece of porous fabric.

15. The sanitizing apparatus as claimed in claim 12, wherein the body portion comprises a front wall, a first sidewall, a second sidewall, and a rear wall, which together form a channel;
the top opening being smaller than the cross-section of the channel.

16. The sanitizing apparatus as claimed in claim 15, wherein at least one of the front wall, the first sidewall, the second sidewall, and the rear wall of the main housing comprises a first slit, and at least one of the front wall, the first sidewall, the second sidewall, and the rear wall of the dispensing member comprises a second slit that is aligned with the first slit.

17. The sanitizing apparatus as claimed in claim 15, wherein at least one of the front wall, the first sidewall, the second sidewall, and the rear wall of the main housing is transparent, and at least a corresponding one of the front wall, the first sidewall, the second sidewall, and the rear wall of the dispensing member is transparent.

18. A sanitizing apparatus comprising:
a main housing;
a dispensing member;
a supporting platform;
a sanitizing fluid pouch;
the main housing comprising a front wall, a first sidewall, a second sidewall, a rear wall, a bottom wall, and an opening;
the front wall, the first sidewall, the second sidewall, the rear wall, the bottom wall of the main housing together forming an internal space accessible through the opening of the main housing;
the dispensing member being inserted into the internal space through the opening of the main housing;
the dispensing member comprising a dispensing mechanism;
the sanitizing fluid pouch being filled with a sanitizing fluid;
the sanitizing fluid pouch being flexible and deformable;
the supporting platform being placed within the dispensing member;
the supporting platform comprising a supporting plate on which is seated the sanitizing fluid pouch;
the supporting platform further comprising a pressure-applying member which is pressed between the supporting plate and the bottom wall of the main housing to apply pressure to the supporting platform and thus the sanitizing fluid pouch;
the dispensing member comprising a top portion, a neck portion, and a body portion;
the top portion comprising a top opening, and the dispensing mechanism being disposed on the top opening;
the neck portion comprising a reduced dimension relative to the body portion;
the body portion comprising a front wall, a first sidewall, a second sidewall, and a rear wall, which together form a channel, the top opening being smaller than the cross-section of the channel.

19. The sanitizing apparatus as claimed in claim 18, wherein the dispensing mechanism is a piece of porous fabric.

20. The sanitizing apparatus as claimed in claim 18, wherein the supporting platform is located inside the channel, and the pressure-applying member is a spring that at one end connects to the supporting plate and at the other end connects to the bottom wall of the main housing.

* * * * *